United States Patent [19]

Nychka et al.

[11]  4,072,726
[45]  Feb. 7, 1978

[54] HYDROGENATION OF FLUORINATED ESTERS

[75] Inventors: Henry Robert Nychka, East Aurora; Richard Elmer Eibeck, Orchard Park; Martin Alvin Robinson, East Amherst; Edward Stephen Jones, Williamsville, all of N.Y.

[73] Assignee: Allied Chemical Corporation, Morris Township, N.J.

[21] Appl. No.: 761,160

[22] Filed: Jan. 21, 1977

[51] Int. Cl.$^2$ .................. C07C 31/34; C07C 29/00
[52] U.S. Cl. .................................. 260/633; 560/197
[58] Field of Search ........................................ 260/633

[56] References Cited

U.S. PATENT DOCUMENTS

| | | | |
|---|---|---|---|
| 2,091,800 | 8/1937 | Adkins et al. | 260/633 |
| 3,324,169 | 6/1967 | Hollander et al. | 260/633 X |
| 3,356,747 | 12/1967 | Anello et al. | 260/633 |
| 3,390,191 | 6/1968 | Anello et al. | 260/633 |
| 3,424,785 | 1/1969 | Pittman et al. | 260/633 X |
| 3,465,050 | 9/1969 | Pittman et al. | 260/633 X |

Primary Examiner—Howard T. Mars
Attorney, Agent, or Firm—Alan M. Doernberg; Jay P. Friedenson

[57] ABSTRACT

Fluorinated esters of the formula $C_nH_xF_{2n+1-x}CO_2CH_2C_mH_yF_{2m+1-y}$ such as $CF_3CO_2CH_2CF_3$ are hydrogenated to fluorinated alcohols such as $CF_3CH_2OH$ using a catalyst having between 50 and 100 percent, and preferably 75-95 percent CuO by weight. In the above formula $n = 1$ to 13, $m = 1$ to 13, $x = 0$ to 3 and $y = 0$ to 3. In the most preferred esters, $n = m$ and $x = y = 0$. The catalyst may also contain 0–50 percent and preferably 5–25 percent by weight of a filler or binder such as a silicate salt. The reaction produces greater yields of alcohol and longer catalyst life than with chromite catalysts, and may proceed at substantially atmospheric pressures.

18 Claims, No Drawings

HYDROGENATION OF FLUORINATED ESTERS

BACKGROUND OF THE INVENTION 2,2,2-trifluoroethanol ($CF_3CH_2OH$) is known to be useful as an intermediate in the formation of the anesthetic $CF_3CH_2OCHF_2$. $CF_3CH_2OH$ is also known to be useful as a working fluid in a Rankine cycle, as disclosed in U.S. Pat. No. 3,722,211. $CF_3CH_2OH$ is also useful as a sovlent in nylon processing. Other fluorinated alcohols are also useful as intermediates.

Commerical processes for producing $CF_3CH_2OH$ usually proceed by oxidation of a perhalogenated ethane, such as $CF_3CCl_3$ to $CF_3COCl$ followed by esterification with $CF_3CH_2OH$ to form $CF_3CO_2CH_2CF_3$ (2,2,2-trifluoroethyl trifluoroacetate) which is then hydrogenated over a catalyst to form 2 moles of $CF_3CH_2OH$ for each mole of ester. One mole of $CF_3CH_2OH$ is recycled to esterify more acid.

This invention is concerned with an improvement in the catalyst performance for the final step of this process, namely the hydrogenation of $CF_3CO_2CH_2CF_3$, preferably at atmospheric pressure. It is also concerned with improved methods of hydrogenation of fluorinated esters generally.

It has previously been reported in U.S. Pat. No. 3,356,747 that a barium promoted copper chromite catalyst could hydrogenate such esters and especially $CF_3CO_2CH_2CF_3$. Typically, the catalyst contains a mixture of 44% CuO, 47% $CrO_3$ and 9% BaO in which the molar ratio of CuO/copper chromite is 0.8/1.0 and BaO is the promoter. Such catalysts, although generally successful, occasionally exhibit the disadvantage of erratic performance and a catalytic life shorter than desired. Thus, prior art processes may require a larger amount of catalyst being used per quantity of fluorinated alcohol and a more frequent replacement of catalyst in the reaction chamber than may be preferred.

Catalysts containing both CuO and $Na_2SiO_3$ are known and are generally used as hydrogenation catalysts for converting aldehydes to alcohols and removing trace amounts of oxygen, carbon monoxide and hydrogen from gas streams. Such a product containing CuO and $Na_2SiO_3$ in varying proportions is manufactured and sold by the Harshaw Chemical Company under the tradename Cu 1710. Use of such a catalyst for ester reductions has not been recommended, based in part upon the work of Adkins et al., *J. Am. Chem. Soc.,* Vol. 72, 2626 (1950), who reported that cupric oxide alone is ineffective in the hydrogenation of esters and that the activity of copper chromite catalysts is dependent upon the ratio of cupric oxide to copper chromite. Adkins postulates that, in the absence of copper chromite, CuO is reduced to copper.

It has thus been suprisingly found according to the present invention, that cupric oxide, in the absence of chromite, is an effective hydrogenation catalyst for certain highly fluorinated esters, and particularly, the hydrogenation of $CF_3CO_2CH_2CF_3$.

BRIEF DESCRIPTION OF THE INVENTION

The invention includes a method for the preparation of fluorinated alcohols of the formula $C_nH_xF_{2n+1-x}CH_2OH$, wherein $n=1$ to 13 and $x=0$ to 3 but not more than $n$, comprising passing at between about 200° C and about a vaporous mixture of hydrogen and a fluorinated ester of the formula $C_nH_xF_{2n+1-x}CH_2CO_2C_mH_yF_{2m+1-y}$, wherein $n$ and $x$ are as described above and $m=1$ to 13 and $y=0$ to 3 but not more than $m$, over a catalyst having by weight about 50 to 100 percent CuO and 0 to about 50 percent by weight of an inert base or binder, said catalyst being essentially free of chromite, and recovering the fluorinated alcohol.

Stated differently, the invention includes an improved method for forming fluorinated alcohols by hydrogenation of fluorinated esters by use of a cupric oxide catalyst in the absence of chromite. In particular, a fluorinated ester having 2-14 carbons in the acid group and 2-14 carbons in the alcohol group is mixed with hydrogen gas in a vaporous mixture and passed over the copper oxide catalyst. In preferred forms, both groups are perfluorinated except for the carboxy carbon and the hydroxy carbon. In preferred forms, the alcohol and acid portions of the ester have identical chain length and halogen substitution such that two moles of a single alcohol are produced from each mole of ester. The most preferred esters are esters of the formula $C_nF_{2n+1}CO_2CH_2C_nF_{2n+1}$ such as $CF_3CO_2CH_2CF_3$. The product alcohol from hydrogenation of the most preferred esters are alcohols $C_nF_{2n+1}CH_2OH$ such as the alcohol $CF_3CH_2OH$.

DETAILED DESCRIPTION OF THE INVENTION

The catalyst used in the process contains about 50–100% cupric oxide, with the remainder being an inert base or binder. In certain preferred forms, the base or binder is a silicate salt such as $Na_2SiO_3$. In preferred forms the catalyst contains by weight about 75–95 percent CuO and about 5–25 percent inert base. In more preferred forms the catalyst contains by weight about 75–90 percent CuO and about 10–25 percent inert base. By "essentially free of chromite" is meant less than 5 weight % chromite, preferably less than 1 weight % chromite and most preferably, free of any detectable chromite.

The reaction vapor mixture contains between about two and about four molecules of hydrogen for each molecule of ester, and preferably about three molecules of hydrogen for each molecule of ester. Under laboratory conditions, over twenty, and in preferred forms over forty grams of alcohol are produced for each gram of catalyst consumed. This is as much as a threefold improvement in performance as compared to tested chromite catalysts.

Hydrogen is reacted with a fluorinated ester such as trifluoroethyl trifluoroacetate in the vapor phase at temperatures of about 200° C to about 325°, and preferably about 225° C to about 275° C. The hydrogenation is catalyzed by a mixture of cupric oxide and an inert base such as $Na_2SiO_3$. The contact time for the hydrogenation may be as long as required for high conversion of ester, about 3 to about 10 seconds for lower esters such as $CF_3CO_2CH_2CF_3$.

The cupric oxide content of the catalyst preferably ranges by weight from about 50 to 100% and most preferably from about 75% to 95%. More than 95% copper oxide is less preferred, not because any loss of catalytic activity, but because of physical problems associated with holding the catalyst together. With a binder such as $Na_2SiO_3$, about 5% binder is adequate to overcome the physical problem, although it should be understood that with other binders, fillers or inert bases, less than 5% may be adequate. Such other carrier can be, for example, fuller's earth, magnesia, silica or alumina may be adequate. 50% CuO, by weight, has been chosen as a preferred minimum because catalytic activity frequently drops off at about that level and frequently drops off below the more preferred minimum of 75% CuO by weight. It should be understood, however, that non-homogeneous catalysts, such as CuO mixed with binder within the preferred range coated on particles of inert carrier would also be preferred, even though CuO might be much less than 50% of the total coated particle weight.

In the experiments that follow this description, the copper catalysts used were activated for hydrogenation by a process proprietary to the Harshaw Chemical Company. While the details of this process are not known, it is believed that careful sintering of the copper oxide may be involved. Copper oxide activated for hydrogenation by the proprietary processes of other companies or by publicly known processes, if any, should produce similar results.

The illustrative reaction

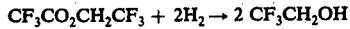

$$CF_3CO_2CH_2CF_3 + 2H_2 \rightarrow 2\ CF_3CH_2OH$$

occurs readily with the conversion of ester ranging up to 99% and the yield being about 95% based on ester converted and is typically about 1 to about 20 seconds, and preferably from 3 to 10 seconds.

The most preferred fluorinated ester used is $CF_3CO_2CH_2CF_3$ to produce $CF_3CH_2OH$ which is a commercially sold intermediate. However, the hydrogenation process has applicability generally to hydrogenation of esters of the formula $$C_nH_xF_{2n+1-x}CO_2CH_2C_mH_yF_{2m+1-y}$$

so as to form the alcohols $C_nH_xF_{2n+1-x}CH_2OH$ and $C_mH_yF_{2m+1-y}CH_2OH$ where $n$ is 1-13, $x$ is 0-3 but not more than $n$, $m$ is 1-13, $y$ is 0-5 but not more than $m$. X and $y$ are limited to 0-3 but no more than $n$ and $m$, respectively, because, even though more hydrogenated esters do react, the CuO catalyst is quickly deactivated as illustrated in Examples 6 and 7.

More preferred are esters in which the alcohol portion and/or the acid portion are perfluorinated except for the carboxy and hydroxy carbons. It is especially preferred that $x=0$, i.e. that the acid portion be perfluorinated. Thus, as examples, preferred 4 carbon esters include $CF_3CO_2CH_2CF_3$, $CHF_2CO_2CH_2CF_3$ and $CF_3CO_2CH_2CHF_2$, preferred 6 carbon esters include $CF_3CF_2CO_2CH_2CF_2CF_3$, $CF_3CHFCO_2CH_2CF_2CF_3$, $CF_3CH_2CO_2CF_2CF_3$, $CF_3CF_2CO_2CH_2CHFCF_3$, $CF_3CF_2CO_2CH_2CH_2CF_3$ and preferred 8 carbon esters include $CF_3(CF_2)_2CO_2CH_2(CF_2)_2CF_3$, $CF_3CF_2CHFCO_2CH_2(CF_2)_2CF_3$, $CF_3(CF_2)_2CO_2CH_2(CF_2)_2CF_3$, $CF_3CF_2CHFCO_2CH_2(CF_2)_2CF_3$, $CF_3(CF_2)_2CO_2CH_2CHFCF_2CF_3$, $CF_3(CF_2)_2CO_2CH_2CH_2CH_2CF_3$ and $CF_3(CF_2)_2CO_2CHFCH_2CF_3$. The more preferred esters are perfluorinated except for the carboxy and hydroxy carbons and can be represented by the formula

$$C_nF_{2n+1}CO_2CH_2C_mF_{2m+1}$$

where $n=1-13$ and $m=1-13$. The alcohols produced by hydrogenation would be $C_nF_{2n+1}CH_2OH$ and $C_mF_{2m}CH_2OH$ where $n$ and $m$ are as described above. Most preferred perfluorinated esters are the symmetrical esters wherein $n=m$ in the immediately preceding three formulas. Exemplary esters of this type include the illustrated ester $CF_3CO_2CH_2CF_3$ as well as such other esters as $CF_3(CF_2)_2CO_2CH_2(CF_2)_2CF_3$, $CF_3(CF_2)_3CO_2CH_2(CF_2)_3CF_3$, $CF_3(CF_2)_6CO_2CH_2(CF_2)_6CF_3$, $CF_3(CF_2)_{10}CO_2CH_2(CF_2)_{10}CF_3$ and $CF_3(CF_2)_{12}CO_2CH_2(CF_2)_{12}CF_3$. The higher fluorinated alcohols $C_nF_{2n+1}CH_2OH$ where $n$ is 5-13 are useful in the preparation of various fluorinated surface active agents.

It will be appreciated that if one of the more preferred esters $C_nF_{2n+1}CO_2CH_2C_mF_{2m+1}$ is hydrogenated according to the present invention to produce $C_nF_{2n+1}CH_2OH$ and $C_mF_{2m+1}CH_2OH$, then the it with $C_nF_{2n+1}COCl$ to generate more ester. With the most preferred ester $C_nF_{2n+1}CO_2CH_2C_nF_{2n+1}$, one-half of the product $C_nF_{2n+1}CH_2OH$ is recycled to react with $C_nF_{2n+1}COCl$ to form the ester without the necessity of any separation.

If one of the less preferred esters of the formula $C_nH_xF_{2n+1-x}CO_2CH_2C_mH_yF_{2m+1-y}$ (wherein $x$ and $y$ are not both 0) is used, then the product alcohols are $C_nH_xF_{2n+1-x}CH_2OH$ and $C_mH_yF_{2m+1-y}CH_2OH$. They must be separated before the $C_mH_yF_{2m+1-y}CH_2OH$ could be recycled to be reacted with fresh $C_nH_xF_{2n+1-x}COCl$ to reform the ester. The net product would be $C_nH_xF_{2n+1-x}CH_2OH$. If $x=0$, then the net product would be perfluorinated except for the terminal carbon, regardless of whether or not the recycled alcohol was perfluorinated (i.e. whether $y=0$). Nonetheless, to avoid separating alcohols, the most preferred esters are those with $n=m$ and $x=y=0$.

It will be appreciated that many such esters can be prepared from the corresponding 1,1,1-trichloro hydrocarbons of the acid portion by a process similar to that used to produce $CF_3CO_2CH_2CF_3$. Thus $C_nF_{2n+1}CCl_3$ can be reacted with $SO_3$ to form $C_nF_{2n+1}COCl$, which is then esterified. It will also be appreciated that when the acid and alcohol portions of the ester have the same carbon chain length and are similarly fluorinated, the alcohol produced from each portion will be identical. This will occur when $n=m$ and $y=x$ with $y$ and $x$ both preferably 0.

The mole ratio of $H_2$/ester can vary from 2/1 to 4/1 or from a stoichiometric amount to a 100% excess, preferably 3/1 or a 50% excess. Contact times can vary from 1 to 20 seconds or preferably from 3 to 10 seconds. Although the catalyst will function at sub or superatmospheric pressure, it is preferred to operate at atmospheric pressure to avoid the cost of vacuum or pressure equipment.

The effluent from the reactor consists of unreacted ester and the product alcohols $C_nH_xF_{2n+1-x}CH_2OH$ and $C_mH_yF_{2m+1-y}CH_2OH$, which in more preferred forms are $C_nF_{2n+1}CH_2OH$ and $C_mF_{2m+1}CH_2OH$, and in most preferred are both $C_nF_{2n+1}CH_2OH$. Using the illustrated $CF_3CO_2CH_2CF_3$ as reactant, the effluent contains unreacted $CF_3CO_2CH_2CF_3$ and product $CF_2CH_2OH$. The alcohol with $m+1$ carbons, or one-half of the homogeneous alcohol product such as $CF_3CH_2OH$ in the illustrated embodiment, is recycled to produce more ester.

In the illustrative embodiment, wherein the ester is $CF_3CO_2CH_2CF_3$, the effluent was condensed by suitable cooling and distilled to give the ester as the lower boiling fraction (b.p. 55°) and $CF_3CF_2OH$ product as the next higher boiling fraction (b.p. 74.5°). In other embodiments, suitable separation techniques, including especially distillation, are employed.

EXAMPLE 1-5

Hydrogenation of $CF_3CO_2CH_2CF_3$

Prior to use, a typical catalyst charge of 150 ml. (10–20 mesh) was conditioned by treating first with $N_2$ at 21 l/h for 3 hours at 200° followed by a mixture of $N_2$ and $H_2$ at 21 l/h and 6 l/h respectively for 19 hours. The reaction was performed in a ½ inch or 1 inch × 20 inch long stainless steel tube. The feed materials were fed upwardly through the tube which was positioned vertically in a temperature controlled fluidized sand bath. Conversion and yield data are based on gas chromatographic analysis of effluent.

Table 1 illustrates the effectiveness of the cupric oxide catalyst in the hydrogenation of trifluoroethyl trifluoroacetate. The average conversion of ester ranged from 54% to 80%. This conversion figure represents moles of product divided by moles of reactant charged (divided by two because each mole of ester produces two moles of alcohol). A measure of catalyst performance is the weight of $CF_3CH_2OH$ produced per unit weight of catalyst consumed. The effects of CuO and $Na_2SiO_3$, different size reactor tubes and different contact times on catalyst activity are cited.

TABLE 1

| EXAMPLE | | 1 | 2 | 3 | 4 | 5 |
|---|---|---|---|---|---|---|
| Catalyst | CuO | 75 | 80 | 80 | 80 | 95 |
| | $Na_2Si_2O_3$ | 25 | 20 | 20 | 20 | 5 |
| ml/gm catalyst | | 50/77 | 50/83 | 50/85 | 150/248 | 50/83 |
| Reactor Size ID | | ½" | ½" | ½" | 1" | ½" |
| Catalyst Temp. ° C. | | 235° | 235° | 235° | 235° | 235° |
| Contact Time in sec. | | 7.2 | 7.6 | 3.6 | 7.2 | 7.2 |
| Ester Flow in moles/hr. | | 0.15 | 0.12 | 0.28 | 0.45 | 0.14 |
| $H_2$ Flow in moles/hr | | 0.45 | 0.45 | 0.90 | 1.35 | 0.45 |
| Catalyst Life in hr. | | 104 | 103 | 53 | 175 | 110 |
| Average Conversion | | 64 | 80 | 54 | 69 | 63 |
| Performance $\frac{CF_3CH_2OH \text{ Produced (gm)}}{\text{Catalyst Consumed (gm)}}$ | | 26/1 | 20/1 | 19/1 | 42/1 | 24/1 |

Yields of $CF_3CH_2OH$ based on ester consumed were generally 95% or higher. This yield figure represents moles of alcohol per mole of ester consumed (divided by two).

EXAMPLES 6 and 7

Under similar reaction conditions butyl trifluoroacetate and ethyl acetate esters are also reduced in the presence of cupric oxide. The extent of conversion and catalyst life, however, are not as favorable as with the trifluoroethyl trifluoroacetate.

EXAMPLE 6

Hydrogenation of Butyl trifluoroacetate

A sample of butyl trifluoroacetate was successfully reduced to $CF_3CF_2OH$ and butanol in the same manner that was used for $CF_3CO_2CH_2CF_3$. A mixture of 0.15 m/h of the ester and 0.45 m/h of $H_2$ was passed through 50 ml. catalyst at 235° for 1.5 hours. The catalyst which was conditioned as in Example 1, prior to use consisted of 80% CuO and 20% $Na_2SiO_3$. A gas chromatographic analysis of the effluent after 1.5 hours of running indicated that 72% of the ester was converted to $CF_3CH_2OH$ and butanol. The catalyst was rapidly deactivated with no conversion detected after 12 hours.

EXAMPLE 7

Hydrogenation of Ethyl Acetate

A sample of ethyl acetate was successfully reduced to ethanol by using a catalyst consisting of 80% CuO and 20% $Na_2SiO_3$ at 235°. During the first hour of running, gas chromatographic analysis indicated a 77% conversion of ester to ethanol. The catalyst was rapidly deactivated with no conversion detected after 10 hours.

EXAMPLE 8

Hydrogenation with Chromite Catalyst

After screening many standard copper chromite catalysts for the hydrogenation of $CF_3CO_2CH_2CF_3$, it was found that Cu1107 (Harshaw), which consisted of 33% CuO, 38% $Cr_2O_3$ and 9% BaO, had a life of 55 hours and gave a performance value of 14/1.

This is significantly lower than obtained with the catalyst of this invention which gives values ranging from 19/1 to 42/1 and has a useful life as long as 175 hours.

EXAMPLES 9–30

Esters are hydrogenated to alcohols using CuO catalysts as illustrated in Table 2. Satisfactory levels of conversion to the alcohols $C_nH_xF_{2n+1-x}CH_2OH$ and $C_mH_yF_{2m+1-y}CH_2OH$ are obtained in each case. In examples 9, 10, 17–23 and 26–30, the alcohol $C_mH_yF_{2m+1-y}CH_2OH$ is recycled to react with the acid chloride $C_nH_2F_{2n+1-x}COCl$ to produce new ester. In examples 11–16, 24 and 25, one-half of the product $C_nF_{2n+1}CH_2OH$ or $C_nH_xF_{2n+1-x}$ is recycled to react with acid chloride $C_nH_2F_{2n+1-x}COCl$ to produce new ester. Such new esters are hydrogenated with the CuO catalyst.

TABLE 2

| | $C_nH_xF_{2n+1}CO_2CH_2$-$C_mH_yF_{2m+1-y}$ ester | | | | Catalyst - By Weight % | | Molar Ratio | Temperature | Contact Time |
|---|---|---|---|---|---|---|---|---|---|
| | n | m | x | y | CuO | Binder | $H_2$/Ester | ° C | seconds |
| 9 | 2 | 1 | 0 | 0 | 100 | — | 3.0 | 200 | 7.0 |
| 10 | 3 | 2 | 0 | 0 | 50 | $Na_2SiO_3$ 50 | 4.0 | 240 | 3.0 |
| 11 | 2 | 2 | 0 | 0 | 95 | $K_2SiO_3$ 5 | 2.0 | 275 | 1.0 |
| 12 | 4 | 4 | 0 | 0 | 90 | $Li_2SiO_3$ 5 | 4.0 | 225 | 5.0 |
| 13 | 6 | 6 | 0 | 0 | 75 | fuller's earth 25 | 4.0 | 275 | 8.0 |
| 14 | 8 | 8 | 0 | 0 | 85 | $Na_2SiO_3$ 15 | 3.5 | 300 | 10.0 |

TABLE 2-continued

| | $C_nH_xF_{2n+1}CO_2CH_2$-$C_mH_yF_{2m+1-y}$ ester | | | | Catalyst - By Weight % | | Molar Ratio | Temperature | Contact Time |
|---|---|---|---|---|---|---|---|---|---|
| | n | m | x | y | CuO | Binder | $H_2$/Ester | °C | seconds |
| 15 | 10 | 10 | 0 | 0 | 75 | $K_2SiO_3$ 25 | 3.1 | 325 | 15.0 |
| 16 | 13 | 13 | 0 | 0 | 75 | magnesia 25 | 3.5 | 260 | 20.0 |
| 17 | 13 | 2 | 0 | 0 | 80 | silica 20 | 3.2 | 270 | 10.0 |
| 18 | 12 | 2 | 0 | 0 | 85 | alumina 15 | 2.8 | 280 | 9.0 |
| 19 | 11 | 1 | 0 | 0 | 80 | $K_2SiO_3$ 20 | 3.0 | 280 | 6.0 |
| 20 | 10 | 1 | 0 | 0 | 80 | $K_2SiO_3$ 20 | 3.0 | 235 | 6.0 |
| 21 | 7 | 3 | 0 | 0 | 80 | $K_2SiO_3$ 20 | 3.0 | 235 | 6.0 |
| 22 | 5 | 1 | 0 | 0 | 80 | $K_2SiO_3$ 20 | 3.0 | 235 | 6.0 |
| 23 | 3 | 1 | 0 | 0 | 80 | $K_2SiO_3$ 20 | 3.0 | 235 | 6.0 |
| 24* | 2 | 2 | 1 | 1 | 80 | $K_2SiO_3$ 20 | 3.0 | 235 | 6.0 |
| 25* | 3 | 3 | 2 | 2 | 80 | $K_2SiO_3$ 20 | 3.0 | 235 | 6.0 |
| 26 | 4 | 1 | 3 | 1 | 80 | $K_2SiO_3$ 20 | 3.0 | 235 | 6.0 |
| 27 | 1 | 4 | 0 | 3 | 80 | $K_2SiO_3$ 20 | 3.0 | 235 | 6.0 |
| 28 | 5 | 1 | 0 | 1 | 80 | $K_2SiO_3$ 20 | 3.0 | 235 | 6.0 |
| 29 | 12 | 2 | 3 | 0 | 80 | $K_2SiO_3$ 20 | 3.0 | 235 | 6.0 |
| 30 | 12 | 2 | 0 | 1 | 80 | $K_2SiO_3$ 20 | 3.0 | 235 | 6.0 |

*The esters of Examples 24 and 25 are $CF_3CHFCO_2CH_2CHFCF_3$ and $CF_3CF_2CH_2CO_2CH_2CH_2CF_2CF_3$.

We claim:

1. A method for the preparation of fluorinated alcohols of the formula $C_nH_xF_{2n+1-x}CH_2OH$, wherein $n=1$ to 13 and $x=0$ to 3 but not more than $n$, comprising passing at between about 200° C and about 325° C a vaporous mixture of hydrogen and a fluorinated ester of the formula $C_nH_xF_{2n+1-x}CO_2CH_2$—$C_mH_yF_{2m+1-y}$, wherein $n$ and $x$ are as described above and $m=1$ to 13 and $y=0$ to 3 but not more than $m$, over a catalyst consisting essentially of about 50 to 100 percent by weight CuO and 0 to about 50 percent by weight of an inert base or binder, said catalyst being essentially free of chromite, and recovering the fluorinated alcohol.

2. A method as claimed in claim 1 wherein the fluorinated ester is passed over the catalyst for about 1 to about 20 seconds contact time.

3. A method as claimed in claim 1 wherein the fluorinated ester is passed over the catalyst at between about 225° C and about 275° C.

4. A method as claimed in claim 2 wherein the contact time is between about 3 seconds and about 10 seconds.

5. The method as claimed in claim 1 wherein the inert base is the silicate salt of an alkali metal.

6. The method as claimed in claim 5 wherein the silicate salt is $Na_2SiO_3$.

7. The method as claimed in claim 1 wherein the fluorinated ester is the ester of a fluorinated acid and a similarly fluorinated alcohol, said acid and alcohol having the same number of carbons, with $n=m$ and $x=y$, whereby the effluent contains as organic materials only unreacted fluorinated ester and an homogenous alcohol product.

8. The method as claimed in claim 1 wherein $x=y=0$.

9. The method as claimed in claim 8 wherein $n=m$.

10. The method as claimed in claim 9 wherein the fluorinated ester is $CF_3CO_2CH_2CF_3$.

11. The method as claimed in claim 1 wherein the molar ratio of hydrogen to ester is between about 2.0:1 and about 4.0:1.

12. The method as claimed in claim 1 wherein the catalyst contains by weight about 75 to about 95 percent CuO and about 5 to about 25 percent inert base, by weight.

13. The method as claimed in claim 1 further including the steps of separating the unreacted fluorinated ester from the fluorinated alcohol product by distillation and reintroducing the unreacted fluorinated ester.

14. The method as claimed in claim 1 wherein the byproduct $C_mH_yF_{2m+1-y}CH_2OH$ is recovered and reacted with the acid chloride $C_nH_xF_{2n+1-x}COCl$ to form the fluorinated ester.

15. The method as claimed in claim 7 wherein a portion of the $C_nH_xF_{2n+1-x}CH_2OH$ homogeneous alcohol product is reacted with the acid chloride $C_nH_xF_{2n+1}COCl$ to form the fluorinated ester.

16. The method as claimed in claim 1 wherein the hydrogenation reaction is conducted at substantially atmospheric pressure.

17. The method as claimed in claim 2 wherein said fluorinated ester is $CF_3CO_2CH_2CF_3$.

18. The method of claim 12 wherein said fluorinated ester is $CF_3CO_2CH_2CF_3$.